(12) United States Patent
Gardner et al.

(10) Patent No.: US 8,320,989 B2
(45) Date of Patent: Nov. 27, 2012

(54) REGION OF INTEREST METHODS AND SYSTEMS FOR ULTRASOUND IMAGING

(75) Inventors: Edward A. Gardner, San Jose, CA (US); Richard M. Kane, Los Altos, CA (US); Joan C. Main, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 889 days.

(21) Appl. No.: 12/234,511

(22) Filed: Sep. 19, 2008

(65) Prior Publication Data

US 2009/0010511 A1    Jan. 8, 2009

Related U.S. Application Data

(62) Division of application No. 10/861,880, filed on Jun. 3, 2004, now abandoned.

(60) Provisional application No. 60/490,324, filed on Jul. 25, 2003.

(51) Int. Cl.
*A61B 5/05* (2006.01)
(52) U.S. Cl. ........................................ 600/407; 382/128
(58) Field of Classification Search .................. 600/407; 382/128
See application file for complete search history.

(56) References Cited

U.S. PATENT DOCUMENTS

| | | | |
|---|---|---|---|
| 4,373,533 A | 2/1983 | Iinuma | |
| 5,235,984 A | 8/1993 | D'Sa | |
| 5,355,887 A | 10/1994 | Iizuka et al. | |
| 5,456,255 A | 10/1995 | Abe et al. | |
| 5,515,856 A | 5/1996 | Olstad et al. | |
| 5,538,003 A | 7/1996 | Gadonniex et al. | |
| 5,615,680 A | 4/1997 | Sano | |
| 5,657,760 A | 8/1997 | Ying et al. | |
| 5,701,897 A | 12/1997 | Sano | |
| 5,743,266 A | 4/1998 | Levene et al. | |
| 5,779,641 A | 7/1998 | Hatfield et al. | |
| 5,785,654 A | 7/1998 | Iinuma et al. | |
| 5,820,561 A | 10/1998 | Olstad et al. | |
| 6,030,344 A | 2/2000 | Guracar et al. | |
| 6,099,471 A | 8/2000 | Torp et al. | |
| 6,174,287 B1 | 1/2001 | Resnick et al. | |
| 6,193,660 B1 | 2/2001 | Jackson et al. | |
| 6,213,945 B1 | 4/2001 | Tynan | |
| 6,217,520 B1 | 4/2001 | He et al. | |
| 6,306,095 B1 | 10/2001 | Holley et al. | |
| 6,346,124 B1 | 2/2002 | Geiser et al. | |
| 6,352,507 B1 | 3/2002 | Torp et al. | |
| 6,360,027 B1 | 3/2002 | Hossack et al. | |
| 6,447,453 B1 | 9/2002 | Roundhill et al. | |
| 6,458,082 B1 | 10/2002 | Jackson et al. | |
| 6,491,636 B2 | 12/2002 | Chenal et al. | |
| 6,500,121 B1 | 12/2002 | Slayton et al. | |

(Continued)

OTHER PUBLICATIONS

Cwajg et al. "Detection of Angiographically Significant Coronary Artery Disease with Accelerated Intermittent Imaging and Intravenous Administration of Ultrasound Contrast Materials," American Heart J. 139: 675-683 (2000).
Wei et al. "Basis for Detection of Stenosis Using Venous Administration of Microbubbles During Myocardial Contrast Echocardiography: Bolus or Continuous Infusion," JACC 32: 252-60 (Jul. 1998).

(Continued)

*Primary Examiner* — Peter Luong

(57) ABSTRACT

A region of interest is identified by user selection of a single point. Multiple regions of interest may be identified by selection of multiple points. Region growing is then used to define the boundary of the region of interest.

20 Claims, 2 Drawing Sheets

U.S. PATENT DOCUMENTS

| | | |
|---|---|---|
| 6,558,325 B1 | 5/2003 | Pang et al. |
| 6,579,240 B2 | 6/2003 | Bjaerum et al. |
| 6,673,017 B1 | 1/2004 | Jackson |
| 6,692,438 B2 | 2/2004 | Skyba et al. |
| 6,884,216 B2 | 4/2005 | Abe et al. |
| 6,980,844 B2 | 12/2005 | Schoisswohl |
| 6,994,673 B2 | 2/2006 | Lysyansky et al. |
| 2002/0103428 A1* | 8/2002 | deCharms ............ 600/410 |
| 2004/0064036 A1 | 4/2004 | Mao et al. |
| 2004/0066389 A1 | 4/2004 | Skyba et al. |
| 2004/0066957 A1 | 4/2004 | Miller et al. |
| 2005/0033123 A1 | 2/2005 | Gardner et al. |
| 2005/0033179 A1 | 2/2005 | Gardner et al. |
| 2008/0027319 A1 | 1/2008 | Gardner et al. |
| 2008/0033294 A1 | 2/2008 | Gardner et al. |
| 2009/0016586 A1 | 1/2009 | Gardner et al. |

OTHER PUBLICATIONS

Wei et al., "Noninvasive Quantification of Coronary Blood Flow Reserve in Humans Using Myocardial Contrast Echocardiography," Circulation 103: 2560-2565 (2001).

Skyba et al., "Methods for Quantitative Analysis," Chapter 4, Handbook of Contrast Echocardiography, pp. 154-171 (Jun. 2000).

"QLAB—Region of Interest (ROI) Quantification," http://www.medical.philips.com/main/products/ultrasound/general/glab/features/roi/, 1 page (printed 2003).

"QLAB Advanced Quantification for Ultrasound," http://www.medical.philips.com/main/products/ultrasound/assets/docs/cardiology/qlab_spec_sheet.pdf, 2 pages (2002).

* cited by examiner

REGION OF INTEREST METHODS AND SYSTEMS FOR ULTRASOUND IMAGING

REFERENCE TO RELATED APPLICATIONS

Related Applications

The present patent document is a divisional of U.S. Published Patent Application No. 20050033123 (Ser. No. 10/861,880), filed Jun. 3, 2004 now abandoned and claims the benefit of the filing date under 35 U.S.C. §119(e) of Provisional U.S. Patent Application Ser. No. 60/490,324, filed Jul. 25, 2003, which are hereby incorporated by reference.

BACKGROUND

The present invention relates to regions of interest in medical imaging. In particular, regions of interest are identified and/or used for generating displays.

Regions of interest are used for various purposes in medical imaging. For example, a region of interest is used in ultrasound imaging for quantifying contrast agent studies. A region of interest is selected in the image. An intensity associated with the region is displayed as a function of time, providing a time-intensity curve. Where multiple regions of interest are identified in an image, separate time-intensity curves are provided.

As an alternative to selecting regions of interest, parametric images are generated. For example, a value is calculated for each pixel based on medical image information. For contrast studies, the value may be associated with an intensity at a given time. Strain, strain rate or other parametric imaging may be provided. Since each pixel is represented in a parametric image, improved spatial resolution is provided. However, a single parametric image may provide little or no information showing a characteristic or value as a function of time. Parametric images may also lack regional based information.

Identifying a region of interest within a medical image may be laborious. Identifying a plurality of regions of interest within an image may be even more laborious. For example, the user traces each region of interest using a user input. Some semi-automated processes may be used for decreasing an amount of time used to designate regions of interest. For example, the user selects a plurality of nodes of points within an image, and a processor uses the nodes to define a region of interest along a border or boundary that passes through the nodes. Edge detection algorithms may be used in a completely automated process. For example, a boundary between the myocardium and a cardiac chamber or the outer edge (i.e. epicardium) is detected. However, automated processes may be inexact. It is important that the regions of interest do not inadvertently include the ventricle in cardiac contrast agent studies to avoid incorrect calculations of perfusion of muscle tissue or the myocardium.

BRIEF SUMMARY

By way of introduction, the preferred embodiments described below include methods and systems for identifying a region of interest and/or for displaying information based on identified regions of interest. In one embodiment, a region of interest is identified by user selection of a single point. Multiple regions of interest may be identified by selection of multiple points. Region growing is then used to define the boundary of the region of interest. In an alternative or additional embodiment, an image processing region is identified by adding additional spatial locations to a region of interest. The image processing region of interest is then used for image processing. In yet another alternative or additional embodiment, information from a plurality of regions of interest is provided in a same frame of reference. For example, an ordered set of regions of interest along the myocardium is defined. An average intensity for each region of interest as a function of time is displayed within the same frame of reference, such as axes of intensity, region of interest number and time. Alternatively, the frame of reference is region of interest and time where a given portion of the image is modulated as a function of the average intensity for the associated region of interest.

Any of the embodiments described herein may be used alone or in combination with other embodiments. For example, regions of interest are automatically identified in response to a user selected point and a display using a single image or same frame of reference for multiple regions of interest is generated.

In a first aspect, a method is provided for displaying region of interest information. At least two regions of interest, each associated with at least two spatial locations, respectively, are identified. A characteristic of each of the at least two regions of interest is determined. A single image representing the characteristics as a function of time for the at least two regions of interest is generated.

In a second aspect, a system is provided for displaying region of interest information. A memory is operable to store data identifying at least two regions of interest. Each of the at least two regions of interest are associated with at least two spatial locations. A processor is operable to determine a characteristic of each of the regions of interest and operable to generate data for a single image representing the characteristics as a function of time for the regions of interest. A display is operable to display the single image.

In a third aspect, a method is provided for identifying a region of interest. A user-selected point is identified. A distance to a boundary from the user-selected point is determined. The region of interest is identified as a function of the user-selected point and the distance.

In a fourth aspect, a system is provided for identifying a region of interest. A memory is operable to stored data identifying a selected point. A processor is operable to determine a distance to a boundary from the selected point and operable to identify the region of interest as a function of the point and the distance.

In a fifth aspect, a method is provided for identifying an image processing region. A region of interest is identified within an image. The image processing region is identified as the region of interest and at least one other spatial location contiguous with the region of interest. Image processing selected from the group of calculating a diagnostic quantity, enhancing the image, enhancing another image, generating a parametric image or combinations thereof is provided based on the image processing region.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In some embodiments, a region of interest is placed by using detected borders for simplification. A point is selected by the user or processor. Boundaries of the region of interest are identified based on the selected point and a distance from one or more boundaries within an image. In other embodiments, a virtual region of interest or an image processing region is identified as a region of interest determined by a user or processor with additional spatial locations in a contiguous grouping. The image processing region of interest is then used for any of various image processes rather than or in addition to the region of interest subset of information. In yet other embodiments, an ordered set of regions of interest are placed in an image. A single display, such as a surface plot or two-dimensional display with color or brightness coding, is used to display within a single frame of reference information from a plurality of regions of interest. For example, time-intensity curves in contrast quantification studies are generated for each of the plurality regions of interest within a single display or frame of reference, displaying a wash-in or wash-out curve for each region of interest at a same time. Any of the embodiments summarized above may be used independently or in any possible combinations. In general, the embodiments will be discussed separately below.

Figure 1:
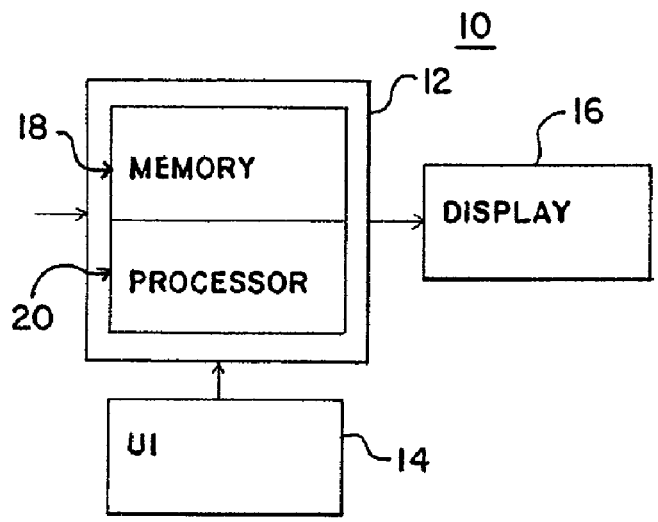
FIG. 1 is a block diagram of one embodiment of a system for use with a region of interest.

FIG. 1 shows a system 10 for identifying a region of interest and/or displaying region of interest information. The system 10 includes image processing system 12, a user interface 14 and a display 16. The image processing system 12 includes a memory 18 and a processor 20. Additional, different or fewer components may be provided in the system 10 or image processing system 12. In one embodiment, the system 10 is a medical diagnostic ultrasound imaging system. In other embodiments, the system 10 is a workstation, computer, network or combinations thereof. The components of the system 10 are provided in a single location, but may be distributed remotely from each other in other embodiments.

The memory 18 is a RAM, ROM, hard drive, removable media, compact disc, DVD, floppy disc, tape, cache memory, buffer, capacitor, combinations thereof or any other now known or later developed analog or digital device for storing information. The memory 18 is operable to store data identifying a selected point for identifying a region of interest. Information from the user interface 14 indicating a position on an image on the display 16 is used to determine a spatial relationship of a user selected point to a scanned region or image position. The selected point is an individual or single point in one embodiment that may be a point selected within a line, area or volume. Additional or different information may be also stored within the memory 18.

The processor 20 is general processor, application specific integrated circuit, digital signal processor, controller, field programmable gate array, digital device, analog device, transistors, combinations thereof or other now known or later developed devices for receiving analog or digital data and outputting altered or calculated data. The processor 20 is a single processor, but may be a distributed processor. The processor 20 is operable to determine a distance from a user-selected point to a boundary. The processor 20 is operable to automatically determine the boundary or is provided with boundary information. For example, the processor 20 is operable to determine a boundary based, at least in part, on a selected point. The boundary is an edge identified using gradient, threshold or other edge detection processes. The edges nearest to the selected point are identified. The processor 20 is also operable to identify a region of interest as a function of a selected point and the distance. For example, a user selects a point in the myocardium of an image. The processor 20 applies an edge detection algorithm to determine the endocardial boundary and/or an epicardium boundary. The shortest distance(s) from the user-selected point to one or both boundaries is determined. The region of interest is then assigned based on the point and the distance(s). For example, the point provides a general position of the region of interest between the boundaries and the distance provides a spatial extent of the region of interest along any dimension. Additional, different or less processing may be performed by the processor 20.

The user input 14 is a track ball, mouse, joy stick, touch pad, buttons, slider, knobs, position sensor, combinations thereof or other now known or later developed input devices. The user input 14 is operable to receive a selected point from a user. For example, the user positions a cursor on an image displayed on the display 16. The user then selects a position of the cursor as indicating a point for a region of interest.

The display 16 is a CRT, LCD, plasma screen, projector, combinations thereof or other now known or later developed devices for displaying an image, a region of interest, region of interest information and/or user input information.

Figure 2:
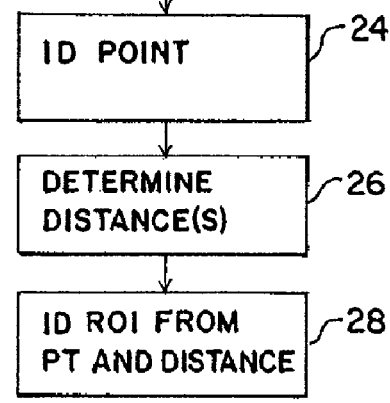
FIG. 2 is a flow chart diagram of one embodiment of a method for identifying a region of interest.

FIG. 2 shows one embodiment of a method for identifying a region of interest. In general, the user selects a point, and a region of interest around the selected point is determined automatically. This semi-automatic region of interest placement may be useful in cardiac contrast quantification where myocardial Perfusion is determined through time intensity curves or other applications. The method uses the system shown in FIG. 1 or a different system. Additional, different or fewer acts may be used in the same or different order than shown in FIG. 2.

In act 24, a point is identified. For example, a single user-selected point for each region of interest within an image is received. As another example, the user inputs a line along a myocardium. Based on an algorithm or user indication, selected points at set distances along the line are user selected points for each of a respective plurality of regions of interest. In alternative embodiments, an automatic or processor-based process is used to identify or select one or more points without user input. In yet other embodiments, the user inputs an area or volume. The user-selected point is then identified as having a particular location relative to the selected area or volume.

For example, the center of the area or volume is used as the user-selected point. By having the user indicate only a single point for a given region of interest, minimal user input is used to identify a region of interest.

In act 26, one or more distances are determined as a function of the selected point. For example, a distance from a user-selected point to a boundary is determined. As another example, a distance between two boundaries passing through the user-selected point is determined. In one embodiment, the distances determined are shortest distances between two boundaries or the shortest distance from the user-selected point to one or more boundaries along the same or different lines. In alternative embodiments, an average distance, a longest distance or other distance is determined.

The boundaries associated with the distance are determined automatically or by user indication. For example, the user traces a boundary. In another embodiment, an edge detection algorithm is applied by a processor to automatically identify one or more boundaries. Any of various edge detection algorithms may be used, such as threshold, gradient, filtering or other now known or later developed edge detection algorithms. In yet other embodiments, a combination of user input and automated detection is used for identifying a boundary. For example, the user indicates one or more locations along a boundary and a processor automatically identifies the rest of the boundary from the user-indicated points. In yet another embodiment, region growing is performed from the user-selected point to identify the distance and the boundary. Using a radial, helical, linear or other search pattern, a shortest distance from the user-selected point to one or more spatial locations associated with an edge or change in pixel values is identified. A threshold or gradient amount of change indicates an edge. For edge detection, a change over a plurality of pixels extending radially away from the selected point or over a single pixel may be used to identify an edge. By growing outward from the user-selected point, a nearest boundary and associated distance from the user-selected point is determined. Additional boundaries may be determined by continuing the search in different directions, such as along an opposite direction. For example, a search region is automatically grown from the user-selected point until the endocardial and epicardial boundaries are detected.

In act 28, a region of interest is identified as a function of the selected point and the distance. For example, the region of interest is identified as a function of the distance from the user-selected point to a single boundary, such as the more easily detected endocardial boundary. As another example, the region of interest is identified as a function of the user-selected point and two distances, such as a distance to each of two boundaries (e.g. endocardium and epicardium boundaries). The two distances are along a same line, but may have different axes in other embodiments.

Figure 5:
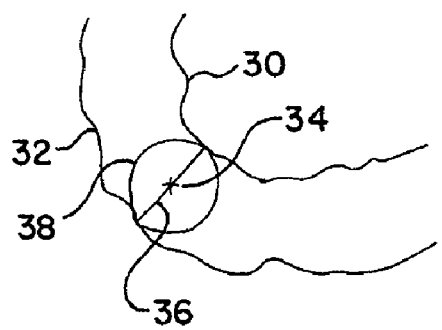
FIG. 5 is a graphical representation of one embodiment of positioning a region of interest based on a selected point.

In one embodiment, a pre-defined shape is positioned around the selected point. A characteristic of the pre-defined shape is a function of one or more distances, such as being equal to or a multiple of the distance(s). For example, a shortest distance between two boundaries passing through the user-selected point is used as a diameter of a circular region of interest. The region of interest is positioned between the boundaries. Other pre-defined shapes may be used, such as rectangle, oval, square or combinations thereof. The distance may be used as any of a radius, circumference, diagonal, length or width, diameter or other characteristic of a shape. For example, FIG. 5 shows the placement of a user-selected point 34 between an endocardium border 30 and an epicardium border 32. The shortest distance between the borders 30 and 32 passing through the point 34 is represented by the line 36. The distance or line 36 is used as a diameter of the circular region of interest 38. The diameter 36 passing through the point 34 provides the position of the region of interest 38 as well as the spatial extent.

While two borders 30, 32 are used as described above, a single border may be used in alternative embodiments. For example, the epicardium may not be easily identified. The distance from the user selected point 34 to the identified endocardium border 32 is determined. The distance is used as a radius. For example, the user is asked to position the selected point 34 at a user perceived center of the myocardium. The user selected point is then used as a center of the region of the region of interest, but may be positioned elsewhere within the region of interest. In another example, the user is asked to position the selected point at the perceived endocardial border 30 for identifying a diameter of the region of interest.

Figure 6:
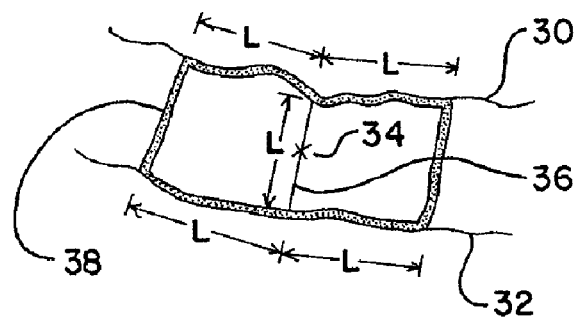
FIG. 6 is a graphical representation of one embodiment of identifying a region of interest from a selected point.

In another embodiment, the distance is used to segment the two boundaries 30 and 32 to identify the region of interest 38. The region of interest 38 has at least part of an extent along one or more of the boundaries 30, 32. For example, in referring to FIG. 6, a distance from a user selected point 34 to a boundary 32 or a distance between two boundaries 30, 32 passing through user selected point 34 is identified. In FIG. 6, the shortest distance between the two boundaries 30 and 32 through the user selected point 34 is represented by L. A segment along one of the boundaries 30, 32 is selected as a function of the distance. For example, a segment having a length L corresponding to the determined distance is drawn along one of the boundaries 30, 32 centered at or extending from the intersection of the distance line 36 with the boundary 30, 32. The region of interest is then identified as at least in part bounded by the segment. As shown in FIG. 6, twice the distance from the user selected point 34 to each of the boundaries 30, 32 is used to select a segment along each of the boundaries 30 and 32. The region of interest 38 is further defined by connecting between the boundaries at the end of the spatial extent of the segments along the boundary 30, 32. In other embodiments, other functions of the length L are used, such as segmenting based on one-half, one-fourth, one, one-and-a half, or other multipliers of the length L.

Where one of the two boundaries 30, 32 is difficult to detect, the segmented region of interest 38 may extend definitively along one boundary. The other boundary is then selected as a function of the determined distance away from the first boundary 32. For example, the other boundary is parallel to and spaced from the boundary 32 at twice a distance from a user selected point 34 to the boundary 32. For example, the user is asked to position the selected point at the half-way point between the perceived boundaries 30, 32. As another example, the distance away from the detected boundary 32 is selected as the distance from the user selected point 34 to the boundary 32 where the user is asked to position the selected point along the perceived difficult to detect boundary. Other distance functions or relations may be used.

Where more than one region of interest is to be identified, the acts 24, 26 and 28 are repeated for each of the regions of interest. For example, a time intensity curve is desired for each of a plurality of regions of interest within a myocardium. A characteristic, such as the average intensity, is determined for each of the regions of interest. The time intensity curves are then displayed separately or together. For example, a single image representing the characteristic as a function of time for each of the plurality of regions of interest is generated as discussed below.

Referring again to FIG. 1, the system 10 may be used for displaying region of interest information. By positioning regions of interest as an ordered set or in a defined pattern, a three-dimensional surface plot or a two-dimensional display with color or brightness coding is used to display information in a same frame of reference for a plurality of regions of interest. For example, a single image is provided representing a wash-in or wash-out curve of contrast agent as a function of time for each of a plurality of regions of interest.

The memory 18 is operable to store data identifying a plurality of regions of interest. Each of the regions of interest is associated with multiple spatial locations rather than being a single sample or pixel location. Regions of interest including at least 25 or more spatial locations may be used. Each spatial location is associated with a pixel or scanning sample. The data identifying the regions of interest is a user selected point in one embodiment. In other embodiments, the data defines other characteristics of the region of interest. The entire region of interest or an identification of each spatial location included within a region of interest is alternatively or additionally stored. The regions of interest may be identified using the processes described above with respect to FIG. 2 or other processes described herein including automated, manual or semiautomatic region of interest determination processes. Further data associated with the region of interest may be stored. For example, labels ordering the regions of interest information into an ordered set are stored. A large number of regions of interest may be stored, such as six or more. Myocardium contrast agent quantification studies may have 10, 12 or other numbers of regions of interest. The regions of interest may overlap or be non-overlapping.

The processor 20 is operable to determine a characteristic of each of the regions of interest identified within the memory 18. For example, the processor 20 determines an average intensity for each region of interest. The processor 20 is operable to generate data for a single image representing the characteristic as a function of time for each of the regions of interest. For example, the time intensity curve for one region of interest is displayed with the time intensity curves for the other regions of interest within a same frame of reference. The processor 20 or the user identifies the same or similar regions of interest throughout a sequence of images, such as using motion tracking, for displaying the characteristic as a function of time.

The display 16 is operable to display a single image representing the characteristic for each of a plurality of regions of interest. For example, the single image represents the characteristic as a function of time for each of at least six or more regions of interest in a same frame of reference. In one embodiment, the single image is provided in a frame of reference of region of interest number as a function of time. Each coordinate or spatial location within the frame of reference is a modulated display value representing the characteristic. Color and/or brightness modulation may be used. In another embodiment, the single image is a three-dimensional surface. The frame of reference is time along one axis, the region of interest along another axis and the characteristic along a third axis. Other images in addition to the single image representing the characteristics for multiple regions of interest may be displayed. For example, the display 16 is operable to display a two-dimensional image or sequence of images simultaneously with the single image for viewing the myocardium or other scanned region at a particular time.

Figure 3:
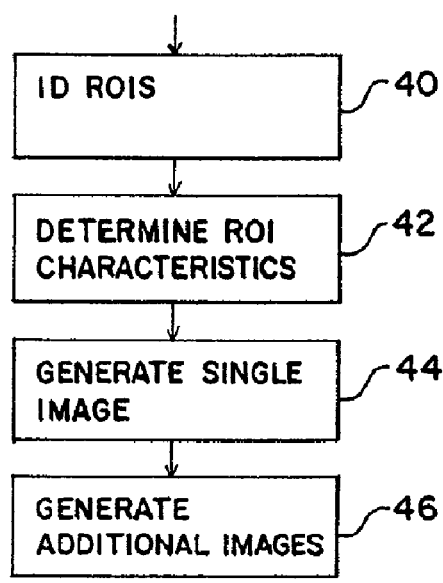
FIG. 3 is a flow chart diagram of one embodiment of a method for displaying region of interest information.

FIG. 3 shows one embodiment of a method for displaying region of interest information. Relative spatial positions of a plurality of regions of interest are used as one parameter within a single image. Time is provided as another parameter. A third parameter within the image is the characteristics determined for each of the regions of interest. A single image with a same frame of reference is provided for representing all of or a plurality of the regions of interest. For example, time-intensity curves for contrast agent quantification studies in cardiology imaging are provided for a plurality of regions of interest at a same time. In alternative embodiments, GI applications, such as liver or kidney imaging, are used. Additional, different or fewer acts may be provided in the same or different order than shown in FIG. 3. The method of FIG. 3 is implemented using the system of FIG. 1 or a different system.

In act 40, at least two regions of interest are identified. For example, 6, 10, 12, or other numbers of regions of interest are identified. The regions of interest overlap or are separate from each other. Overlapping and regions of interest not overlapping with other regions of interest may be provided in a same set of regions of interest in a same image. Each of the regions of interest is a same size, but different size regions of interest may be used in other embodiments. Each region of interest extends over at least two spatial locations. For example, regions of interest with at least 25 spatial locations are used. Regions of interest with hundreds of spatial locations, such as associated with a 10×10 square region of interest, may be used. Two-dimensional regions of interest within a two-dimensional image are identified. In other embodiments, three-dimensional regions of interests associated with three-dimensional images or representations are identified.

Manual, semiautomatic or automatic identification of the regions of interest in a multidimensional image is provided. For example, a user selects a point associated with each of a plurality of regions of interest. The regions of interest are then identified as regions surrounding the selected points, such as discussed above with respect to FIG. 2. Other semi-automatic identification of the regions may be used. Alternatively, the regions of interest are automatically placed without user input. As yet another alternative embodiment, one or more of the regions of interest are entirely manually defined by the users. Combinations of automatic, semiautomatic or manual placement may be used for different ones of the regions of interest within a set of regions of interest.

The regions of interest are placed in a pattern. For example, the regions of interest are labeled as a function of spatial location or as a function of the order of determination or identification. In one embodiment, the regions of interest are placed in a myocardium successively around the left ventricle starting from one portion of the myocardium and extending to another portion. The process is performed automatically. Alternatively, the user indicates a line extending along the myocardium. Regions of interest are then semi-automatically placed at set intervals along the line. For example, the set intervals are used to identify user selected points for determining the regions of interest as discussed above for FIG. 2. In yet another embodiment, an endocardium or other detected boundary is used for determining the relative positions of the plurality of regions of interest. The regions of interest are successively placed along the boundary, such as to one side or extending over both sides of a boundary. The order of the regions of interest within a set is intuitive, such as a function of position along the myocardium. Alternatively or additionally, each of the regions of interest is labeled with a number, letter or other designator different for each of the regions of interest.

In act 42, a characteristic is determined for each of the regions of interest. A characteristic of data from each, all, a sub-set, or one of the spatial locations associated with a region of interest is calculated. For example, time intensity curves of the average intensity using contrast agent detection techniques for each of the regions of interest is determined. This average intensity could be normalized in some way, for example by the beginning or ending value. The regions of interest are automatically, semi-automatically or manually determined for each of a plurality of images in a sequence of images. The average intensity or other contrast agent related quantity for each region of interest as a function of time represents the wash-in, wash-out or other characteristic of contrast agent perfusion. The characteristic is calculated for each of the regions of interest.

Figure 7:
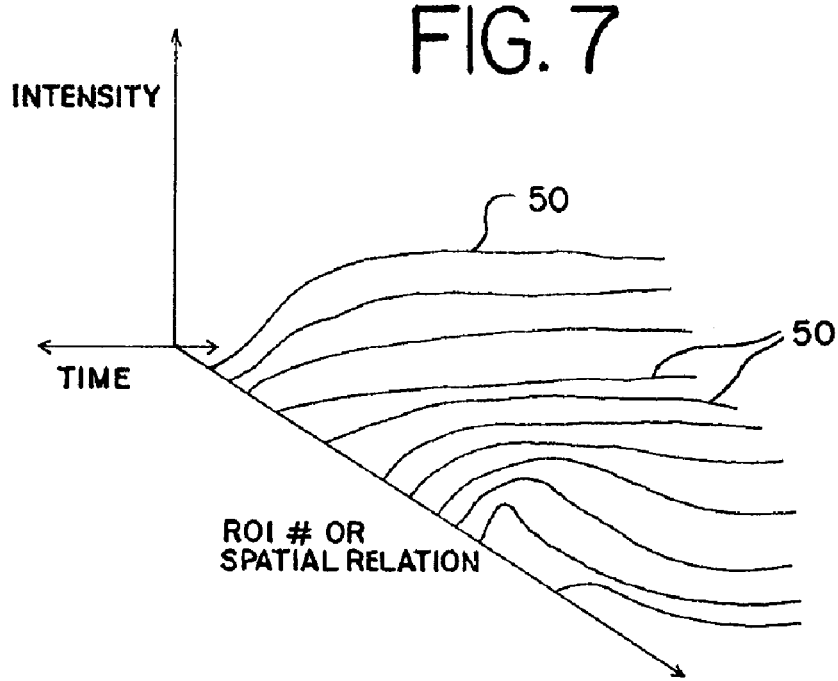
FIG. 7 is a graphical representation of a three-dimensional surface representation for displaying a region of interest information.

In act 44, a single image representing the characteristic from multiple regions of interest is generated. For contrast agent or other applications, the single image represents the characteristic as a function of time. For example, the characteristic as a function of time is provided for each of six or more regions of interest. The single image provides the characteristic for each of the regions of interest within a same frame of reference. For example, a single image representing a three-dimensional display is provided. A three-dimensional surface represents the characteristic along one axis, such as an average intensity axis, the region of interest along another axis, such as an axis representing a region of interest label number or a region of interest distance along the user designated line or detected boundary, and a third axis representing time. FIG. 7 shows one embodiment of the single image where three axes are provided as a same frame of reference. The plurality of lines 50 shows intensity as a function of time for different regions of interest. The lines 50 are presented as a three-dimensional surface. By viewing the single image, the user may understand what portion of the myocardium has unusual flow given the spatial relationship or region of interest labels. If the regions of interest overlapped, smoothing of the time intensity surface provided by the lines 50 is provided. Other surface renderings or three-dimensional representations based on the same or similar information may be provided.

Figure 8:
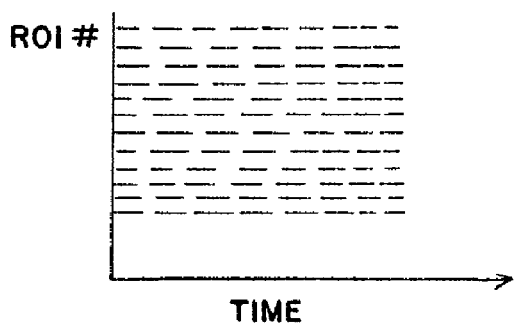
FIG. 8 is a graphical representation of another embodiment of a two-dimensional display of region of interest information.

In another embodiment, the single image is a two-dimensional display of the characteristic as a modulated value. For example, FIG. 8 shows a frame of reference as the region of interest number or relative spatial location along one axis and time along another axis. For each coordinant within the two-dimensional frame of reference, the characteristic of the associated region of interest at a given time modulates the brightness and/or color of the displayed data. The strip display is similar to a strain rate display or m-mode display. Since each characteristic value is a function of a plurality of spatial locations for a region of interest, the display is similar to an m-mode image with a large amount of spatial filtering or smoothing. Since different ROI sizes and shapes may be used, anisotropic filtering is provided.

Using either of the types of displays described above with reference to FIGS. 7 and 8 or a different display representing a single image, information from a plurality of regions of interest is provided. At a given time, the single image represents information for a plurality of regions of interest for at least one time in a same frame of reference. The given single image may represent the characteristic for each of the regions of interest for a plurality of previous times. As additional information becomes available from subsequent imaging, the single image is updated or regenerated. The additional information is added to the previous single image. All of the information from the previous calculations or images is maintained, but some information may be dropped.

In act 46, an additional image is generated substantially simultaneously with the single image. "Single" image is used herein as a display of data from multiple regions of interest in one image as opposed to in separate images or frames of reference. The additional image is a two- or three-dimensional representation of the scanned region at a particular time. As the single image is updated, the additional image is changed to represent a current scan of the region. For example, a B-mode or B- and flow-mode image is displayed adjacent to the single image representing characteristics of the regions of interest.

Figure 4:
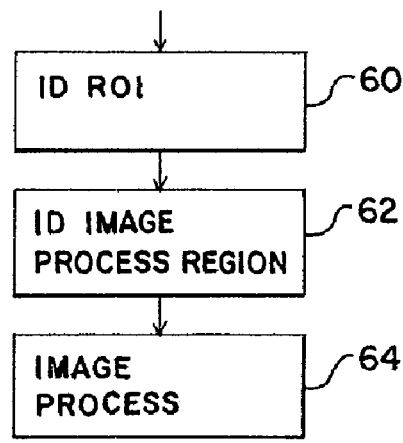
FIG. 4 is a flow chart diagram of one embodiment of a method for identifying an image processing region.

FIG. 4 shows one embodiment of a method for identifying an image processing region. One or more regions of interest on an image designate areas of importance to a user. To avoid processing an entire image, including image data outside of the user designated areas, an image processing region including the regions of interest is identified. A virtual super-region of interest is determined and image processing is restricted to or performed differently for the virtual super-region of interest to increase speed of processing but with sufficient information. The system shown in FIG. 1 or other systems may be used. Additional, different or fewer acts may be provided in the same or different order than shown in FIG. 4.

In act 60, a region of interest is identified within an image. One, two or more regions of interest are identified within a same image, such as a B-mode image. The regions of interest are identified manually, semi-automatically or automatically as discussed herein.

In at 62, an image processing region is identified as including the region of interest and at least one other spatial location contiguous with the region of interest. For example, an image processing region boundary surrounding all of the user selected regions of interest within an image is identified. The image processing region does not include the entire image. In one embodiment, a predetermined shape is applied with a size sufficient to surround all the users selected regions of interest with a user or predetermined threshold margin or minimum margin. Any of various shapes may be used. Rather than a predetermined shape, the image processing region may have a set margin around user selected regions of interest. Where image processing regions associated with different regions of interest do not intersect or overlap, separate image processing regions are provided or they are combined together, such as smoothly transitioning along a shortest distance location between the regions of interest and associated image processing regions. Alternatively, the size of the margin is increased in order to cause a threshold amount of overlap.

In one embodiment, the image processing region or regions are visually displayed to the user to indicate size, shape and location. The user may reset variables used to determine the image processing region for redetermination or may adjust the image processing region in order to include other landmarks or anatomy. For example, the user clicks on a point adjacent to the image processing region, and the boundary of the image processing region is transitioned to include the selected point with smooth variation.

In act 64, image processing is performed based on the image processing region. Any of various image processors may be used. For example, a diagnostic quantity is calculated from data associated with the image processing region. The data selected includes data from the regions of interest as well as the additional contiguous spatial locations. Another image process may be enhancement of the image, such as to reduce the speckle, increase contrast or combinations thereof. The enhancement of the images may be provided for the image processing region. Alternatively or additionally, data associated with the image processing region is used to determine a threshold, algorithm or other variable used for enhancing a subsequent image. The other image is adaptively enhanced based on the image processing region. Additionally, or alternatively, a parametric image is generated for the image processing region. For example, the strain, strain rate, time-intensity or combinations thereof are generated for the image processing region. Any one of the image processes are performed for a given image processing region. In alternative embodiments, any combination of two or more of the processes is performed for the image processing region.

The areas outside of the image processing region are either displayed or not displayed during or after image processing performed for the image processing region. For example, the areas outside of the image processing region are masked out. As another example, the areas outside the image processing region are displayed but are not subjected to the image processing performed within the image processing region.

In another embodiment, the image processing region is used for motion tracking between images within a sequence. The image processing region is used to define a search region or to define a pattern for searching within a subsequent image. The regions of interest are then identified in subsequent images based on searches performed within the spatial extent of the image processing region. The regions of interest are then tracked or shown as moving within the image processing region through a series of images. The regions of interest may be tracked for registering the images relative to each other, such as for forming an extended field of view. Data outside the imaging processing region is displayed and translated or rotated based on the movement detected within the image processing region. Alternatively, the data outside the region is displayed but is not shown as moving or is not translated or rotated. The image processing region of interest allows excluding undesired structure or fluids, such as the chest wall, from motion estimation to make estimates more accurate. For example, motion tracking of liver or other deep tissue studies is provided without adverse influence by lesser moving intervening tissues, such as skin and muscle.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for identifying a region of interest, the method comprising:
    (a) identifying a user selected point of a location represented by scan data;
    (b) determining, by a processor, a first distance associated with a first boundary and the user selected point, the first boundary being a tissue boundary represented by the scan data and spaced from the location such that the tissue boundary is used to determine the first distance; and
    (c) identifying, by the processor, the region of interest as a function of the user selected point and the first distance such that a size of the region of interest is based on the first distance.

2. The method of claim 1 further comprising:
    (d) determining the first boundary with the processor, the first boundary based, at least in part, on the user selected point.

3. The method of claim 1 further comprising:
    (d) determining a second distance to a second boundary different than the first boundary;
    wherein (c) comprises identifying the region of interest as a function of the user selected point, the first distance and the second distance.

4. The method of claim 3 wherein (c) comprises:
    (c1) selecting a first segment along the first boundary as a function of the first and second distances;
    (c2) selecting a second segment along the second boundary as a function of the first and second distances;
    (c3) identifying the region of interest at least in part as bounded by the first and second segments.

5. The method of claim 1 wherein (c) comprises positioning a predefined shape around the user selected point wherein the size of the predefined shape is a function of the first distance.

6. The method of claim 5 wherein the predefined shape comprises a square, a rectangle, an oval, a circle or combinations thereof and the size comprises a radius, a circumference, a diagonal, a length or a width.

7. The method of claim 1 wherein (c) comprises:
    (c1) selecting a first segment along the first boundary as a function of the first distance; and
    (c2) identifying the region of interest at least in part as bounded by the first segment.

8. The method of claim 1 further comprising:
    (d) repeating (a), (b) and (c) for each of at least two regions of interest;
    (e) determining a size of each of the at least two regions of interest; and
    (f) generating a single image representing the size as a function of time for each of the at least two regions of interest.

9. The method of claim 1 wherein (a) comprises identifying a single user selected point for each single region of interest.

10. A system for identifying a region of interest, the system comprising:
    a memory operable to store data identifying a selected point of a location in an image of the patient, the selected point spaced away from a first boundary, the first boundary being a tissue boundary in the image of the patient; and
    a processor operable to determine a first distance to the first boundary from the selected point and operable to identify the region of interest as a function of the selected point and the first distance.

11. The system of claim 10 further comprising:
    a user input operable to receive the selected point from a user.

12. The system of claim 10 wherein the processor is operable to automatically determine the first boundary based, at least in part, on the selected point.

13. The system of claim 12 wherein the selected point comprises a user selected point.

14. The system of claim 10 wherein the processor is operable to determine a second distance to a second boundary different than the first boundary and wherein the processor is operable to identify the region of interest as a function of the user selected point, the first distance and the second distance.

15. The system of claim 10 wherein the processor is operable to identify the region of interest by selecting a first segment along the first boundary as a function of the first and second distances, selecting a second segment along the second boundary as a function of the first and second distances, and identifying the region of interest at least in part as bounded by the first and second segments.

16. The system of claim 10 wherein the processor is operable to identify the region of interest by positioning a predefined shape around the user selected point wherein a characteristic of the predefined shape is a function of the first distance.

17. The system of claim 16 wherein the predefined shape comprises a square, a rectangle, an oval, a circle or combinations thereof and the characteristic comprises a radius, a circumference, a diagonal, a length or a width.

18. The system of claim 10 wherein the processor is operable to identify the region of interest by selecting a first segment along the first boundary as a function of the first distance, and identifying the region of interest at least in part as bounded by the first segment.

19. The system of claim 10 wherein the processor is further operable to repeat determining and identifying for each of at least two regions of interest, determine a characteristic of each of the at least two regions of interest, and generate a single image representing the characteristic as a function of time for each of the at least two regions of interest in a same frame of reference with common axes.

20. The system of claim 19 wherein the single image represents the characteristic as a modulated display value as a function of time and region of interest.

* * * * *